(12) United States Patent
Ruiz, Sr. et al.

(10) Patent No.: US 8,550,737 B2
(45) Date of Patent: Oct. 8, 2013

(54) APPLICATORS FOR DISPENSING ADHESIVE OR SEALANT MATERIAL

(75) Inventors: Rafael Ruiz, Sr., Hudson, NC (US); Sheng Zhang, Granite Falls, NC (US); Martin Krauss, Fort Myers, FL (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 412 days.

(21) Appl. No.: 12/886,070

(22) Filed: Sep. 20, 2010

(65) Prior Publication Data
US 2012/0070220 A1  Mar. 22, 2012

(51) Int. Cl.
*B43K 5/14* (2006.01)
(52) U.S. Cl.
USPC .............................. 401/134; 604/3; 401/133
(58) Field of Classification Search
USPC ................. 401/132–135; 604/3; 606/214
See application file for complete search history.

(56) References Cited

U.S. PATENT DOCUMENTS

| | | |
|---|---|---|
| 211,104 A | 1/1879 | Mulford |
| 334,046 A | 1/1886 | Pinkham |
| 1,221,227 A | 4/1917 | Schulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 3,152,352 A | 10/1964 | Kosik, Jr. |
| 3,254,111 A | 5/1966 | Hawkins et al. |
| 3,324,855 A | 6/1967 | Heimlich |
| 3,393,962 A | 7/1968 | Andrews |
| 3,523,628 A | 8/1970 | Colvin et al. |
| 3,614,245 A | 10/1971 | Schwartzman |
| 3,797,706 A | 3/1974 | Mule |
| 3,924,623 A | 12/1975 | Avery |
| 3,941,488 A | 3/1976 | Maxwell |
| 3,945,383 A | 3/1976 | Bennett et al. |
| 4,138,040 A | 2/1979 | Stock |
| 4,199,915 A | 4/1980 | Levine |

(Continued)

FOREIGN PATENT DOCUMENTS

| | | |
|---|---|---|
| DE | 203 14 688 U1 | 11/2003 |
| EP | 1 445 032 | 8/2004 |

(Continued)

OTHER PUBLICATIONS

International Search Report and Written Opinion for corresponding international application No. PCT/US2011/051762 dated Nov. 30, 2011.

(Continued)

*Primary Examiner* — David Walczak
*Assistant Examiner* — Jennifer C Chiang
(74) *Attorney, Agent, or Firm* — Stradley Ronon Stevens & Young, LLP

(57) ABSTRACT

An applicator device for storing and dispensing an adhesive or sealant material, which are compatible with irradiation sterilization techniques, the applicator comprising: an applicator body comprising a cutting portion to break the frangible seal of the container for the adhesive, and a grasping and squeezing portion for controlling the flow rate of the adhesive; a container for an adhesive material that is movable relative to the applicator body and is made of materials with high barrier property; and a porous applicator tip that is secured to or frictionally fits into the applicator body.

17 Claims, 5 Drawing Sheets

(56) References Cited

U.S. PATENT DOCUMENTS

| | | | |
|---|---|---|---|
| 4,271,982 A * | 6/1981 | Niksich et al. | 222/83 |
| 4,408,699 A | 10/1983 | Stock | |
| 4,413,753 A * | 11/1983 | Stock | 222/149 |
| 4,480,940 A | 11/1984 | Woodruff | |
| 4,498,609 A | 2/1985 | Stock | |
| 4,507,111 A * | 3/1985 | Gordon et al. | 604/3 |
| 4,685,591 A | 8/1987 | Schaefer et al. | |
| 4,687,827 A | 8/1987 | Russo | |
| 4,724,177 A | 2/1988 | Russo | |
| 4,772,148 A | 9/1988 | Buschemeyer | |
| 4,777,085 A | 10/1988 | Murray, Jr. et al. | |
| 4,784,506 A | 11/1988 | Koreska et al. | |
| 4,844,250 A | 7/1989 | Holoubek et al. | |
| 4,979,638 A | 12/1990 | Bolduc | |
| 5,006,004 A | 4/1991 | Dirksing et al. | |
| 5,016,784 A | 5/1991 | Batson | |
| 5,018,643 A | 5/1991 | Bolduc | |
| 5,031,384 A | 7/1991 | Rebeyrolle et al. | |
| 5,042,690 A * | 8/1991 | O'Meara | 222/83 |
| 5,052,585 A | 10/1991 | Bolduc | |
| 5,131,777 A | 7/1992 | Kimura et al. | |
| 5,133,458 A | 7/1992 | Miller | |
| 5,154,320 A | 10/1992 | Bolduc | |
| 5,171,149 A | 12/1992 | Alpert | |
| 5,226,562 A | 7/1993 | Kirk | |
| 5,232,774 A | 8/1993 | Otsuka et al. | |
| 5,263,615 A | 11/1993 | Anderson et al. | |
| 5,288,159 A | 2/1994 | Wirt | |
| 5,324,131 A * | 6/1994 | Gardner, III | 401/199 |
| 5,344,670 A | 9/1994 | Palmer et al. | |
| 5,358,349 A * | 10/1994 | Burroughs et al. | 401/184 |
| 5,379,927 A | 1/1995 | Montenieri et al. | |
| 5,411,345 A | 5/1995 | Ueji et al. | |
| 5,649,648 A | 7/1997 | Lier et al. | |
| 5,658,384 A | 8/1997 | Imlay, Jr. | |
| 5,665,106 A | 9/1997 | Hammerslag | |
| 5,665,107 A | 9/1997 | Hammerslag | |
| 5,749,665 A | 5/1998 | Kato et al. | |
| 5,759,194 A | 6/1998 | Hammerslag | |
| 5,769,552 A * | 6/1998 | Kelley et al. | 401/132 |
| 5,810,495 A | 9/1998 | McAuley | |
| D402,199 S | 12/1998 | Saunders | |
| 5,888,007 A | 3/1999 | Nicoll et al. | |
| 5,906,300 A | 5/1999 | Horie | |
| 5,909,976 A | 6/1999 | Maeda | |
| 5,928,611 A | 7/1999 | Leung | |
| 5,971,225 A | 10/1999 | Kapsa | |
| 5,996,796 A | 12/1999 | Kvitrud et al. | |
| 6,099,807 A | 8/2000 | Leung | |
| 6,136,326 A | 10/2000 | Kotzev | |
| 6,155,265 A | 12/2000 | Hammerslag | |
| 6,217,603 B1 | 4/2001 | Clark et al. | |
| 6,248,800 B1 | 6/2001 | Greff et al. | |
| 6,283,933 B1 | 9/2001 | D'Alessio et al. | |
| 6,322,852 B1 | 11/2001 | Leung | |
| 6,331,172 B1 | 12/2001 | Epstein et al. | |
| 6,340,097 B1 | 1/2002 | D'Alessio et al. | |
| 6,372,313 B1 | 4/2002 | D'Alessio et al. | |
| 6,376,019 B1 | 4/2002 | Leung | |
| 6,425,704 B2 | 7/2002 | Voiers et al. | |
| 6,428,233 B1 | 8/2002 | Clark et al. | |
| 6,428,234 B1 | 8/2002 | Bobo et al. | |
| 6,439,789 B1 | 8/2002 | Ballance et al. | |
| 6,475,502 B1 | 11/2002 | Lee et al. | |
| 6,478,191 B1 | 11/2002 | D'Alessio et al. | |
| 6,488,665 B1 * | 12/2002 | Severin et al. | 604/200 |
| 6,492,434 B1 | 12/2002 | Barley, Jr. et al. | |
| 6,494,896 B1 | 12/2002 | D'Alessio et al. | |
| 6,505,985 B1 * | 1/2003 | Hidle et al. | 401/134 |
| 6,506,464 B1 | 1/2003 | Montenieri et al. | |
| 6,541,304 B1 | 4/2003 | Bouras et al. | |
| 6,547,467 B2 | 4/2003 | Quintero | |
| 6,550,644 B2 | 4/2003 | Cruddas | |
| 6,557,731 B1 | 5/2003 | Lyon et al. | |
| 6,592,281 B2 | 7/2003 | Clark et al. | |
| 6,595,940 B1 | 7/2003 | D'Alessio et al. | |
| 6,616,019 B2 | 9/2003 | D'Alessio et al. | |
| 6,637,967 B2 | 10/2003 | Bobo et al. | |
| 6,672,456 B2 | 1/2004 | Russell | |
| 6,676,322 B1 | 1/2004 | Leung | |
| 6,676,332 B1 | 1/2004 | Hauer et al. | |
| 6,705,467 B1 | 3/2004 | Kancsar et al. | |
| 6,705,790 B2 | 3/2004 | Quintero et al. | |
| 6,779,657 B2 | 8/2004 | Mainwaring et al. | |
| 6,802,416 B1 | 10/2004 | D'Alessio et al. | |
| 6,811,341 B2 | 11/2004 | Crane | |
| 6,817,802 B2 | 11/2004 | Nishitani et al. | |
| 6,863,460 B2 | 3/2005 | Nicoll et al. | |
| 6,960,040 B2 | 11/2005 | D'Alessio et al. | |
| 6,981,664 B1 | 1/2006 | Fugere | |
| 7,040,827 B2 | 5/2006 | Gueret | |
| 7,094,250 B2 | 8/2006 | Stenton | |
| 7,128,241 B2 | 10/2006 | Leung | |
| 7,179,008 B2 | 2/2007 | Holcomb | |
| 7,297,217 B2 | 11/2007 | Dewitt | |
| 7,306,390 B2 * | 12/2007 | Quintero et al. | 401/133 |
| RE40,003 E | 1/2008 | Bennett et al. | |
| 7,316,833 B1 | 1/2008 | Galloway et al. | |
| 7,441,973 B2 | 10/2008 | Voegele et al. | |
| 7,516,872 B2 | 4/2009 | Boone et al. | |
| 7,621,411 B2 | 11/2009 | Doherty et al. | |
| 7,648,296 B2 * | 1/2010 | Wong | 401/134 |
| 7,696,399 B2 | 4/2010 | Rogers | |
| 7,704,003 B2 | 4/2010 | Ziniti et al. | |
| 7,708,180 B2 | 5/2010 | Murray et al. | |
| 7,744,624 B2 | 6/2010 | Bettuchi | |
| 7,785,026 B2 | 8/2010 | Eng et al. | |
| 8,118,508 B2 * | 2/2012 | Goodman et al. | 401/133 |
| 8,198,344 B2 * | 6/2012 | Zhang et al. | 522/79 |
| 2002/0151873 A1 | 10/2002 | Moore | |
| 2005/0025559 A1 | 2/2005 | Stenton | |
| 2005/0047845 A1 | 3/2005 | White et al. | |
| 2005/0047846 A1 | 3/2005 | Narang et al. | |
| 2005/0054967 A1 | 3/2005 | Ashe et al. | |
| 2005/0147457 A1 | 7/2005 | Badejo et al. | |
| 2005/0147582 A1 | 7/2005 | Zimmerman et al. | |
| 2005/0148998 A1 | 7/2005 | Haley | |
| 2005/0175395 A1 | 8/2005 | Quintero et al. | |
| 2005/0196431 A1 | 9/2005 | Narang et al. | |
| 2005/0197421 A1 | 9/2005 | Loomis | |
| 2005/0256446 A1 | 11/2005 | Criscuolo et al. | |
| 2006/0049203 A1 | 3/2006 | Boone et al. | |
| 2006/0247568 A1 * | 11/2006 | Stenton | 604/3 |
| 2006/0282035 A1 | 12/2006 | Battisti et al. | |
| 2007/0078207 A1 | 4/2007 | Jonn et al. | |
| 2007/0084144 A1 | 4/2007 | Labrecque et al. | |
| 2007/0131356 A1 | 6/2007 | Battisti | |
| 2007/0147947 A1 | 6/2007 | Stenton et al. | |
| 2008/0021139 A1 | 1/2008 | Blacklock et al. | |
| 2008/0033280 A1 | 2/2008 | Lubock et al. | |
| 2008/0058863 A1 | 3/2008 | Quintero et al. | |
| 2008/0069801 A1 | 3/2008 | Lee et al. | |
| 2008/0095569 A1 | 4/2008 | Voegele et al. | |
| 2008/0105580 A1 | 5/2008 | Nentwick et al. | |
| 2008/0121657 A1 | 5/2008 | Voegele et al. | |
| 2008/0125811 A1 | 5/2008 | Bettuchi | |
| 2008/0131190 A1 | 6/2008 | Goodman et al. | |
| 2008/0167681 A1 | 7/2008 | Stenton | |
| 2008/0195040 A1 | 8/2008 | Clark et al. | |
| 2008/0241249 A1 | 10/2008 | Quintero et al. | |
| 2008/0287987 A1 | 11/2008 | Boyden et al. | |
| 2009/0257976 A1 | 10/2009 | Kerber et al. | |
| 2009/0311030 A1 | 12/2009 | Stenton | |
| 2009/0317353 A1 | 12/2009 | Zhang et al. | |
| 2009/0318583 A1 | 12/2009 | Zhang et al. | |
| 2009/0324319 A1 | 12/2009 | Houde et al. | |
| 2009/0324320 A1 | 12/2009 | Houde et al. | |
| 2010/0168637 A1 | 7/2010 | Casey et al. | |
| 2010/0168638 A1 | 7/2010 | Korogi et al. | |

(56) References Cited

U.S. PATENT DOCUMENTS

2010/0274258 A1    10/2010    Silvestrini et al.
2011/0028883 A1    2/2011    Juan, Jr. et al.

FOREIGN PATENT DOCUMENTS

| | | |
|---|---|---|
| FR | 1130737 | 10/1956 |
| FR | 2700698 | 7/1994 |
| GB | 1016053 | 1/1966 |
| JP | 58-41068 | 3/1983 |
| JP | 2006-315307 | 11/2006 |

OTHER PUBLICATIONS

Quinn, J.V., "Clinical Approaches to the Use of Cyanoacrylate Tissue Adhesives", Tissue Adhesives in Clinical Medicine, Second Edition, 2005, BC Decker, Inc., pp. 27-76.

Canale, A.J., et al., "Methyl a-cyanoacrylate. I. Free-radical homopolymerization", Journal of Applied Polymer Science, vol. 4, No. 11, Sep./Oct. 1960, pp. 231-236 [Abstract Only].

* cited by examiner

APPLICATORS FOR DISPENSING ADHESIVE OR SEALANT MATERIAL

BACKGROUND OF THE INVENTION

The present invention is directed to single-use disposable applicators for applying liquid materials. More particularly, the present invention relates to single-use applicators for applying a polymerizable material such as cyanoacrylate monomers as surgical adhesives, sealants and dressings.

Various dispensing and packaging systems for cyanoacrylate-based adhesive and/or sealant material have been proposed. U. S. Pat. Appl. Pub. No. 20080167681 to Stenton discloses an adhesive applicator for applying medical adhesives to surgical incisions. The applicator comprises a receiver having a deformable cylindrical body, a blunt cylindrical body with an adhesive-permeable foam material, a frangible ampule containing adhesive material, and a pair of wings having a pressure barb facing toward the cylindrical wall to break the frangible ampule.

U.S. Pat. Appl. Pub. No. 20080105580 to Nentwick et al. discloses an applicator tip for dispensing a cyanoacrylate-based adhesive from a reservoir. The applicator tip includes an opening offset and a distal end. The adhesive material is dispensed when pressure is applied to the applicator tip surface so that the applicator tip is in a deformed configuration.

U.S. Pat. Appl. Pub. No. 20070147947 to Stenton et al. discloses an applicator for forming uniform thickness layers of liquid coating on a substrate surface. The applicator is characterized by controlling the dispensing of liquid through apertures incorporated within the applicator head. The applicator uses a supported thin layer of foam which assures uniform thickness of applied layers, which are substantially independent of the pressure applied to the applicator.

U.S. Pat. Appl. Pub. No. 20060282035 to Battisti et al. discloses a disposable swab applicator for containing and dispensing cyanoacrylate adhesive. The swab applicator is closed at one end and covered by a swab applicator with the cyanoacrylate composition contained by a valve that can be easily opened when desired. The valve can be a ball, a bead or a capsule.

The device can be heat sterilized using dry heat sterilization.

U.S. Pat. No. 7,297,217 to Dewitt discloses a dispenser for application of a special low viscosity cyanoacrylate adhesive which is used for the manufacture and repair of wooden furniture. The dispenser is provided with a closure member having a metallic pin which penetrates into the discharge opening while the closure member is being secured thereon. U.S. Pat. No. 6,779,657 to Mainwaring et al. discloses a single-use applicator assembly for applying and dispensing cyanoacrylate monomeric adhesive material. The applicator comprises a base with at least one sealed container and an applicator tip at least partially disposed in the container such that the tip of the applicator has access to the adhesive material. U.S. Pat. No. 6,547,467 to Quintero discloses a microapplicator for dispensing and applying cyanaocrylate-based adhesive. The microapplicator comprises a handle portion, a microerservoir at the applicator tip to hold about 20 microliter or less, of adhesive material. The applicator tip may include a spatula, a rolling ball, a grate, a porous material, and a brush. U.S. Pat. No. 5,649,648 to Lier et al. discloses a packaging system for free-flowing material such as cyanoacrylate adhesive. The package comprises a container and a closable applicator point fitted on its outlet aperture. The container is made of an extruded receptacle aluminum which springs back when the pressure is released. U.S. Pat. No. 4,685,591 to Schaefer et al. discloses a packaging tube that is suitable for storing and dispensing products containing substantial fractions of cyanoacrylates. The tube sidewall is made of multi-layer sheet material and a covering strip is placed over the inside surface the tube. U.S. Pat. No. 4,413,753 to Stock discloses a self-draining tip for dispensing cyanoacrylate adhesives. The dispensing tip includes a single or segmented constant diameter passageway having sharp-edged annular terminations for dispensing.

Closure Medical Corporation prepared and published a series of patents in terms of applying and dispensing cyanoacrylate adhesives. For example, U.S. Pat. Appl. Pub. No. 20050175395, U.S. Pat. Nos 7,306,390 and 6,705,790 to Quintero et al. discloses an applicator assembly for dispensing adhesive material. The applicator comprises first and second body portions, a frangible ampule container for adhesive, and a breaking member to rupture the container for dispensing the adhesive material. U.S. Pat. Nos 6,960,040, 6,494, 896, and 6,340,097 to D'Alessio et al. disclose package assembly suitable for laparoscopic or endoscopic surgery. U.S. Pat. Nos 7,128,241, 6,676,322, 6,376,019, 6,322,852, 6,099,807, 5,928,611 to Leung discloses an applicator tip for dispensing cyanoacrylate adhesive stored in a frangible glass ampule container. The porous, absorbent applicator tip includes a polymerization initiator to accelerate the polymerization of cyanoacrylate adhesive when applied. The DERMABOND® applicator associated with most patents mentioned above comprises a glass ampule for storing adhesives and a porous applicator tip incorporating a polymerization initiator. As published by FDA in the Maude Adverse Event Report, the glass vial of the DERMABOND® applicator was crushed and the shard protruded through the tube, penetrated the gloves and pierced the hands of the medical professionals or the patients. The shard penetration adverse effect of DERMABOND® occurred repeatedly since it was marketed. The breakage or rupture of broken glass through the outside plastic package exposes the user or patient to risk. Another problem associated with this type of applicator is the clogging of the applicator tip. The presence of polymerization initiator in the applicator tip can lead to rapid polymerization of cyanoacrylate adhesives to clog the applicator, which causes the waste of adhesive material. The clogging of the applicator may delay the wound closure process during surgery, which may result in problems for both patients and surgical professionals.

Besides safety and the clogging problem, the prior applicator devices exhibit other shortcomings. The lack of flow rate control of adhesive is one of the issues surgical doctors often face. A further inconvenience which has occurred in prior applicators is the requirement of two hands to operate. Furthermore, the design and dispensing mechanism of some of the prior applicators are very complicated and thereby very expensive. More importantly, the known applicators fail to be compatible with irradiation sterilization techniques so that cyanoacrylate adhesives inside either cannot be sterilized by irradiation sterilization, such as electron beam, gamma, and X-ray, or cannot provide a stable shelf life after sterilization in such applicator. Therefore, a need exists for new applicator designs, which are easy to use, safe due to the absence of glass, capable of controlling flow rate, compatible with irradiation sterilization techniques, exhibits no clogging of the applicator tip, and causes no waste of adhesives.

SUMMARY OF THE INVENTION

This invention provides applicators which address the need for an easy to use, safe and efficient package system for applying and dispensing an adhesive material, preferably a cyanoacrylate-based medical adhesive.

In one aspect, the invention provides applicators to store and apply an adhesive material safely, conveniently, controllably, and effectively. The applicators include an applicator body, a container of adhesive material, and an applicator tip. The applicator tip includes at least one absorbent portion for absorbing adhesive to be applied.

The present invention provides applicators which are designed to be compatible with irradiation sterilization techniques such as gamma sterilization, electron beam sterilization and X-ray sterilization so that adhesive stored in said applicators can be sterilized by irradiation sterilization. The containers of the applicators for adhesive materials comprising acrylonitrile copolymer or multi-layer sheet materials with acrylonitrile copolymer as the inner layer. The exceptional barrier properties offered by acrylonitrile copolymer make it an ideal material for use in construction of package bodies for storing and sterilizing cyanoacryalte-based adhesives in accordance with the present invention. The adhesives packaged in said applicators are therefore able to be sterilized by irradiation sterilization techniques, and are not cured upon sterilization. More desirably, the adhesive packaged in applicators disclosed in the present invention provides a long term shelf life stability of at least 12 months, and more preferably of at least 24 months after sterilization by irradiation sterilization techniques.

Various applicators disclosed herein are designed to store, sterilize, and apply adhesive compositions. The adhesive compositions are preferably polymerizable 1,1-disbustituted ethylene monomers, and more preferably the adhesive compositions are based on cyanoacrylate monomers.

In one embodiment, the present invention provides an applicator device for storing and dispensing an adhesive material. The applicator comprises a container for an adhesive material that is movable within the applicator wherein the container comprises a frangible seal for containing the adhesive material; and a body portion comprising: a porous applicator tip, a cutting portion to break the frangible seal thus allowing flow of the adhesive towards the porous applicator tip, a flexible portion for controlling the flow rate of the adhesive, and a finger stopper.

In another embodiment, the present invention provides an applicator device for storing and dispensing an adhesive material. The applicator body has a cutting portion affixed inside the body. The applicator body is also equipped with a finger stopper on the outside wall for user's convenience to activate the applicator. The container for the adhesive material is movable relative to the applicator body. The applicator tip is designed to friction fit into the applicator body. The applicator tip fits tightly into the applicator body so that no leak of the adhesive occurs during use. The applicator is also equipped with a finger stopper portion in order to facilitate activating the applicator and dispensing the adhesive by hand for user's convenience. The flow rate of adhesive packaged in said applicator may be controlled by providing a constant but slow pressure on the griping section of the applicator body.

In preferred embodiments, the container is made of acrylonitrile copolymer or multi-layer sheet material with acrylonitrile copolymer as the contact layer to the adhesive. The container is preferably further equipped with a frangible membrane, which is heat sealed onto the container. Movement of the container relative to the applicator body causes the cutting portion to break the frangible membrane of the container so that the adhesive can be released and dispensed onto the applicator tip, to be applied.

In another embodiment, an applicator comprises an applicator body, a cutting device, a container, a container mount, and an applicator tip. The applicator tip is tightly attached to the applicator body using a screw cap or snap-fit connection. The open end of the container is sealed with a frangible membrane. In order to be compatible with irradiation sterilization techniques, the container is preferably made of acrylonitrile copolymer or multi layer sheet materials with acrylonitrile copolymer as the inner layer. The container of the adhesive is movable relative to the cutting device that is affixed to the inner wall of the applicator body. As the adhesive container is pushed into the applicator body, the frangible membrane of the container is pierced by the cutting device. The adhesive is then released through the opening and into the channel inside the applicator body and dispensed onto the applicator tip for application. A grasping portion is designed at the end close to the applicator tip for both holding the applicator and controlling the flow rate of the adhesives. The grasping portion comprises semi-rigid material to permit controlled flow of the adhesive to the application site.

In another embodiment of the present invention, an applicator device comprises both an applicator tip and an applicator body. The applicator tip includes an applicator cap to seal the opening of the applicator tip. The applicator body contains an air space reducer and a reservoir container to store the adhesive. The applicator is activated when the applicator cap is twisted or pulled off from the applicator tip so that the adhesive saturated on the tip can be applied. A squeezing portion that is made of semi-rigid material is designed on the applicator body in order to control the flow rate of the adhesive during use. The reservoir container for the adhesive comprises at least one material with a high barrier property such as, for example, an acrylonitrile copolymer.

BRIEF DESCRIPTION OF THE DRAWINGS

FIG. 2 is a perspective view of the component parts of the applicator embodied by

FIG. 1;

FIG. 6 is a perspective view of the component parts of the applicator embodied by

FIG. 5;

DETAILED DESCRIPTION OF EXEMPLARY EMBODIMENTS

Figure 1:
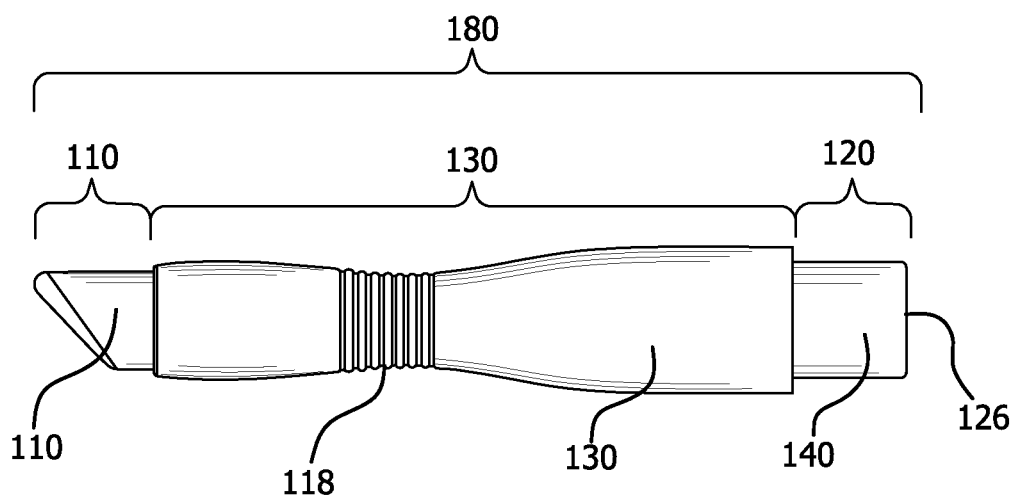
FIG. 1 is a perspective view of a first exemplary applicator of this invention.
Figure 2:
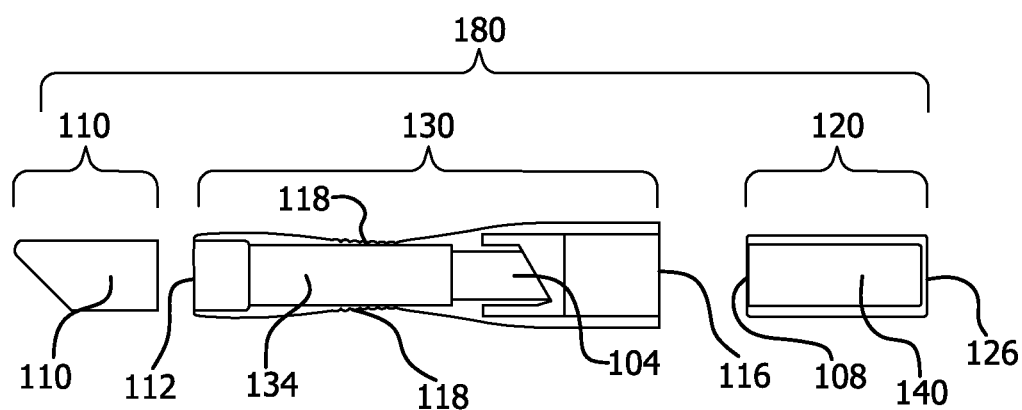
Figure 3:
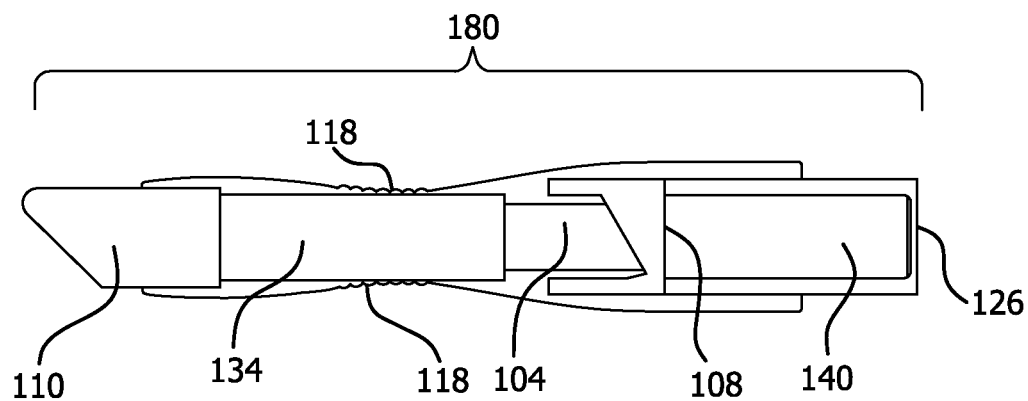
FIG. 3 is a cross-sectional view of the exemplary embodiment of FIG. 1.

In embodiments of the present invention, an applicator comprises an applicator device body, a container for adhesive material, and an applicator tip. Adhesive material is prepackaged in the dispenser in a container sealed by a frangible membrane or by at least one hermetically sealed membrane. The container for adhesives can be prepared by multi-layer sheet material and the inner layer that contacts adhesives can be, but is not limited to, acrylonitrile copolymer. The container thereby constructed is compatible with irradiation sterilization techniques, such as, for example, electron beam, gamma or X-ray sterilization, so that adhesives inside the applicator can be sterilized via such irradiation techniques. The long-term shelf life stability of adhesive packaged in said applicators may be provided after irradiation sterilization.

FIGS. 1-4 represent views of embodiments of the present invention. As shown in FIGS. 1-4, applicator 180 comprises an applicator tip 110, an applicator body 130, and a container 120. The container 120 is movable within a chamber 116 relative to the applicator body 130. The chamber 116 houses the container 120 and is in fluid communication with a channel 134. The applicator 180 is activated by pushing the end 126 of the container 120 towards the cutting portion 104 of the applicator body 130. While moving the container 120 into the applicator body 130, the cutting portion 104 cuts through the frangible membrane 108 on the container 120, and adhesive 140 inside the container 120 is released into the channel 134. The adhesive 140 is then dispensed through the open end of the applicator body 130 onto the applicator tip 110, which is how the adhesive is applied onto the substrate.

The applicator body 130, including the cutting portion 104 and the channel 134, may be constructed from any suitable materials. In a more preferred embodiment, the applicator body may be made of a material that can prevent or reduce the premature polymerization of adhesive materials.

The applicator tip 110 is designed to friction fit into the open end 112 of the applicator body 130. The applicator tip 110 fits tightly into the applicator body so that no leak occurs during dispensing of the adhesive. The applicator tip may be a fibrous swab, a sponge swab, a foam tip, or a brush. The applicator tip may be composed of any of a variety of materials including foams, sponges, rubber, plastics, thermosets, films or membranes. The foam material may be but not limited to polyolefin foam, polyether polyurethane foam, polyester polyurethane foam, and so forth.

The flow rate of adhesive 140 may be controlled by providing a constant but slow pressure on the griping section 118 of the applicator body 130. In embodiments, a desired amount of adhesive can be dispensed by applying a desired force to the griping section 118.

The applicator container 120 has a volume of about 0.1 mL to 20 mL, preferably about 0.2 mL to 15 mL, and more preferably about 0.2 mL to 10 mL. In order to inhibit the premature polymerization, the volume of the applicator is preferably about 50 to 80 percent, and more preferably 60 to 80 percent, filled by the adhesive.

The cutting portion 104 is designed to be sharp and strong so as to readily break the frangible membrane 108 for dispensing adhesive 140 inside the container 120. Suitable materials for the cutting portion 104 include but not limited to high density polyethylene (HDPE), polypropylene, polyvinylchloride, polycarbonate, polytetrafluoroethylene (PFTE), polyethylene terephthalate (PET), polystyrene (PS), and polymethylpentene.

Figure 4:
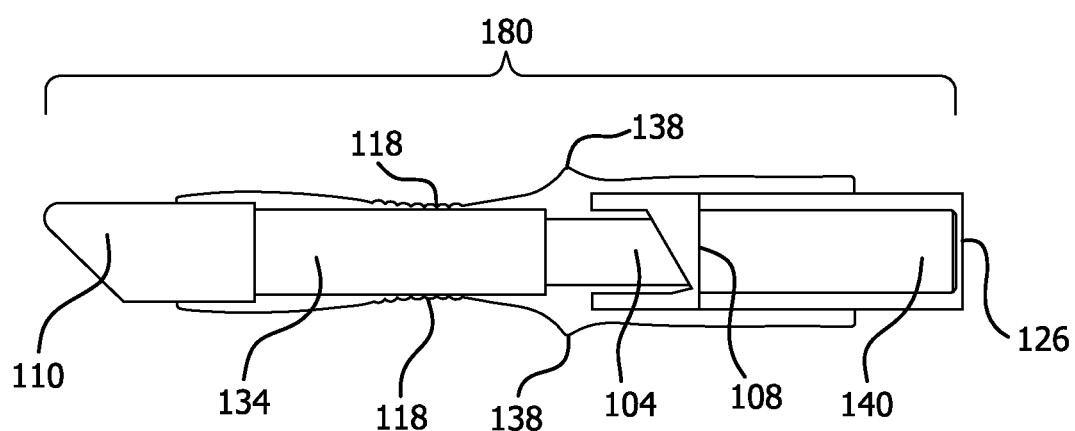
FIG. 4 is cross-sectional view of another embodiment of the present invention.

In order for the user's comfort to hold and activate the applicator 180, a finger stopper 138 is added to the applicator body 130, as shown in another cross-sectional view of a first embodiment of the present invention (FIG. 4). The user may use his/her index and middle fingers to hold the finger stopper 138, while use his/her thumb to push the end 126 of the container 120 for the activation of the applicator 180.

The frangible membrane 108 is heat sealed to the container 120 for storing adhesive 140. Suitable materials for the frangible membrane 108 may include, but are not limited to, aluminum foil, plastic membrane, laminated aluminum foil, plastic wrap, waxed paper, oiled paper, or the like. Laminated aluminum foil may be composed of at least two layers of different materials which include, but are not limited to, aluminum, acrylonitrile copolymer, low density polyethylene, low density polypropylene, polyethylene teraphthalate, and the like. In a preferred embodiment, laminated aluminum foil with acrylonitrile copolymer as the inner layer is used to construct the frangible membrane 108.

Suitable materials for the container 120 should have a desired barrier property for moisture and air so that the premature polymerization of adhesive 140 can be prevented or inhibited. Suitable materials for the container 120 include, but are not limited to, high density polyethylene (HDPE), polypropylene, polyvinylchloride, acrylonitrile copolymer, polycarbonate, polytetrafluoroethylene (PFTE), and polyethylene terephthalate (PET), and the like. In a preferred embodiment, the container 120 is made of multi-layer sheet material with acrylonitrile copolymer as the inner layer. In another preferred embodiment, the entire container 120 is made of an acrylonitrile copolymer except the frangible membrane 108.

Suitable acrylonitrile copolymer used to construct the container 120 and the inner layer of the frangible membrane 108 include acrylonitrile copolymers produced by polymerizing a major proportion of a monounsaturated nitrile and a minor proportion of another monovinyl monomer or indene copolymerizable nitrile polymers produced by polymerizing a major portion of a monounsaturated nitrile and a minor portion of another monovinyl monomer or indene copolymerizable therewith in the presence of a diene rubber, polyacarylates, polymethoactrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile. Preferred acrylonitrile copolymers include copolymer of acrylonitrile and methyl acrylate, which is a product commercially available from BP America under the trademark of Barex®.

Acrylonitrile copolymer used to construct the container 120 provides high barrier properties which ensure the stability of the cyanoacrylate adhesive 140 stored therein. Acrylonitrile copolymer offers a high barrier to oxygen at all levels of relative humidity. This ensures that a consistently high barrier to oxygen is maintained, regardless of the humidity of the surrounding environment. In addition, the water vapor barrier properties of acrylonitrile copolymer make it a desirable material for packaging and sterilizing cyanoacrylate-based adhesive materials in accordance with the present invention.

As disclosed herein, the adhesive 140 in the container 120 constructed with acrylonitrile copolymer itself, or multi-layer sheet materials with acrylonitrile copolymer as the inner layer, can be sterilized by irradiation sterilization techniques such as gamma sterilization, electron beam sterilization and X-ray sterilization. The said applicator 180 is compatible with those irradiation sterilization techniques so that the adhesive 140 is not cured upon the irradiation sterilization. The adhesive 140 sterilized by irradiation sterilization in the applicator 180 may provide long term shelf life stability of at least 12 months and more preferably at least 24 months.

Figure 5:
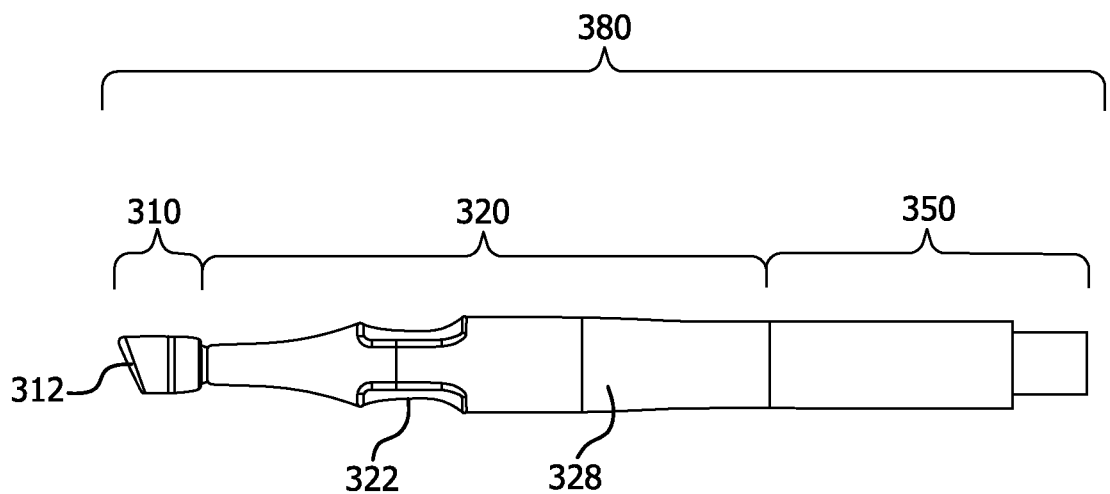
FIG. 5 is a perspective view of another embodiment of the present invention.
Figure 6:
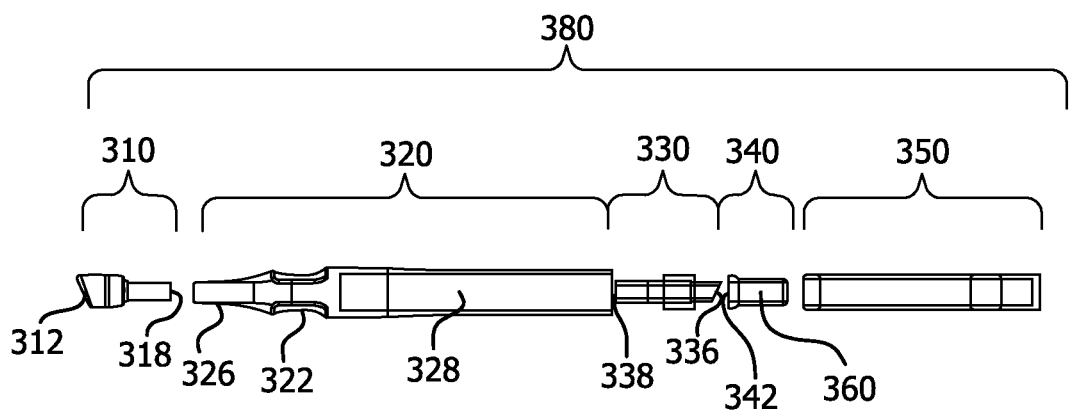
Figure 7:
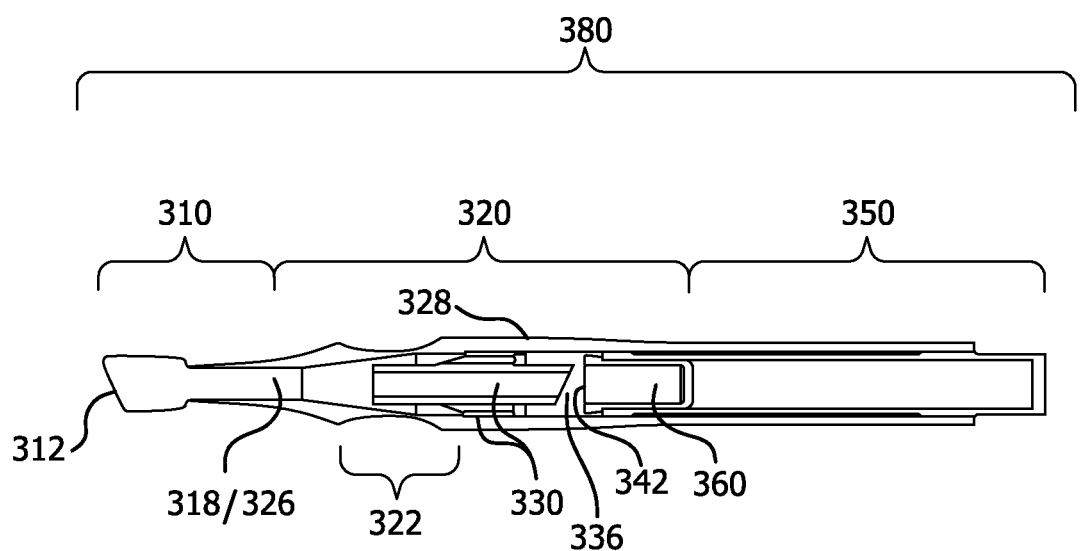
FIG. 7 is a cross-sectional view of the exemplary embodiment of FIG. 5.

FIGS. 5-7 illustrate another embodiment of the present invention. In this embodiment, applicator 380 comprises an applicator tip 310, an applicator body 320, a cutting device 330, a container 340, a container mount 350. The container 340 attached onto the container mount 350 is movable relative to the cutting device 330 that is affixed to the inner wall of the applicator body 320. A grasping portion 322 is placed on the applicator body 320 near to the applicator tip 310.

The applicator body 320 has an open end 326, which can be used to connect the applicator tip 310 and the body through the open end 318 of the applicator tip using, for example, a screw cap or snap-fit connection. The tight connection between the applicator tip 310 and the applicator body 320 is designed to prevent a leak of the adhesive 360 stored in the container 340. The applicator body 320 comprises an open end 326, a grasping portion 322, and a reservoir 328 onto which a cutting device 330 is affixed as shown in FIGS. 6 and 7. The cutting device 330 has two open ends to connect the container 340 and the opening channel inside the applicator body, through which the adhesive 360 can be delivered to the applicator tip 310 during the activation of the applicator 380. The container 340 is either permanently affixed or frictionally fit onto the container mount. A frangible membrane 342 is used to seal the container 340, which can be cut through by the cutting device 336 when the container 340 is moving toward to the applicator body 320 during activation.

To activate the applicator 380, a user pushes the container mount 350 which holds the container 340 using his/her thumb while holding the applicator body with hand. As the container 340 is pushed into the applicator body 320, the cutting device 330 cuts the frangible membrane 342 through and moves into the container 340. The adhesive 360 is then released through the channel inside the applicator body 320 and dispensed onto the applicator tip 310 for application.

The open end 326 of the applicator body is equipped with a screw cap or snap cap, in which the applicator tip 310 is tightly attached to the applicator body 320. The tight connection between the applicator tip 310 and the applicator body 320 is designed to prevent leakage of the adhesive 360 during the application process. The applicator tip may be a fibrous swab, a sponge swab, a foam tip, or a brush. The applicator tip may be composed of any variety of materials including, but not limited to foams, rubber, plastics, thermosets, films or membranes. The foam material may be, but is not limited to polyolefin foam, polyether polyurethane foam, polyester polyurethane foam, and the like.

The grasping portion 322 of the applicator body 320 is designed for both holding the applicator and controlling the flow rate of the adhesive. For convenience and comfort, a user may hold the grasping portion 322 as a pen with his/her thumb and index finger when using the applicator to apply adhesive. The flow rate of adhesive 360 may be controlled by providing a constant but slow pressure on the grasping portion 322 of the applicator body 320. In embodiments, the desired amount of adhesive can be dispensed by applying the desired force to the grasping portion 322. The grasping portion is generally made of semi-rigid material to permit controlled flow of the adhesive to the application site via change in pressure. Suitable materials include, but are not limited to, rubber, thermoplastics, thermosets, low density polyethylene, polypropylene, medium density polyethylene, high density polyethylene, or polyesters.

In certain embodiments, the applicator body 320 may be constructed from any suitable materials. In a more preferred embodiment, the applicator body may be made of a material that can prevent or reduce the premature polymerization of adhesive materials. Referring to FIG. 6, the exemplary cutting device 330/336 is designed to be sharp and rigid so as to readily break the frangible membrane 342 for dispensing adhesive 360 stored in the container 340. Still referring to FIG. 6, cutting device 336 is angled and hollow so the liquid adhesive can flow there through once the membrane is pierced. Suitable materials for the cutting device 330 include, but are not limited to, high density polyethylene (HDPE), polypropylene, polyvinylchloride, polycarbonate, polytetrafluoroethylene (PFTE), polyethylene terephthalate (PET), polystyrene (PS), a polymethylpentene, and the like.

As described herein, the frangible membrane 342 is heat sealed onto the container 340 after pre-packaging the adhesive 360 into the container 340. The frangible membrane has to be easily breakable so that the cutting device 330 can readily cut through it for dispensing adhesive inside the container. At the same time, the frangible membrane should also possess a desired barrier property for moisture and air in order to effectively sterilize and store the adhesive 360. Suitable materials for the frangible membrane 342 may include, but are not limited to, aluminum foil, plastic membrane, laminated aluminum foil, plastic wrap, waxed paper, oiled paper, or the like. Laminated aluminum foil may be composed of at least two layers of different materials which include, but are not limited to, aluminum, acrylonitrile copolymer, low density polyethylene, low density polypropylene, polyethylene teraphthalate, and the like. In a more preferred embodiment, laminated aluminum foil with acrylonitrile copolymer as the inner layer is used to construct the frangible membrane 342.

Fill volume of the applicator container 340 is in the range of about 0.1 mL to 20 mL, preferably about 0.2 mL to 15 mL, and more preferably about 0.2 mL to 10 mL. In order to inhibit the premature polymerization, the volume of the applicator is preferably about 50 to 80 percent and more preferably 60 to 80 percent filled by the adhesive. The container 340 may be constructed with suitable materials that have a desired barrier property for moisture and air so that the premature polymerization of adhesive 360 can be prevented or inhibited. Suitable materials for the container 340 include, but are not limited to, high density polyethylene (HDPE), polypropylene, polyvinylchloride, acrylonitrile copolymer, polycarbonate, polytetrafluoroethylene (PFTE), and polyethylene terephthalate (PET), and the like. In a preferred embodiment, the container 340 is made of multi-layer sheet material with acrylonitrile copolymer as the inner layer. In another preferred embodiment, the entire container 340 is made of a thick layer of acrylonitrile copolymer. Suitable acrylonitrile copolymers used to construct the container 340 include those described previously in the first embodiment of the present invention.

In certain embodiments of the present invention, the applicator illustrated by FIGS. 5-7 may also include another detachable or replaceable tip (not shown) over the applicator tip 310. The detachable or replaceable tip is narrower in dimension compared to the applicator tip 310 for a more precise application of the adhesive 360 to the application site.

In a particular embodiment, the adhesive 360 in the container 340 comprising acrylonitrile copolymer can be sterilized by irradiation sterilization techniques such as gamma sterilization, electron beam sterilization and X-ray sterilization. The said applicator 380 is compatible with irradiation sterilization techniques so that the adhesive 360 is not cured upon the irradiation sterilization. The adhesive 360 sterilized by irradiation sterilization in the applicator 380 may provide long term shelf life stability of at least about 12 months, and more preferably at least about 24 months.

Figure 8:
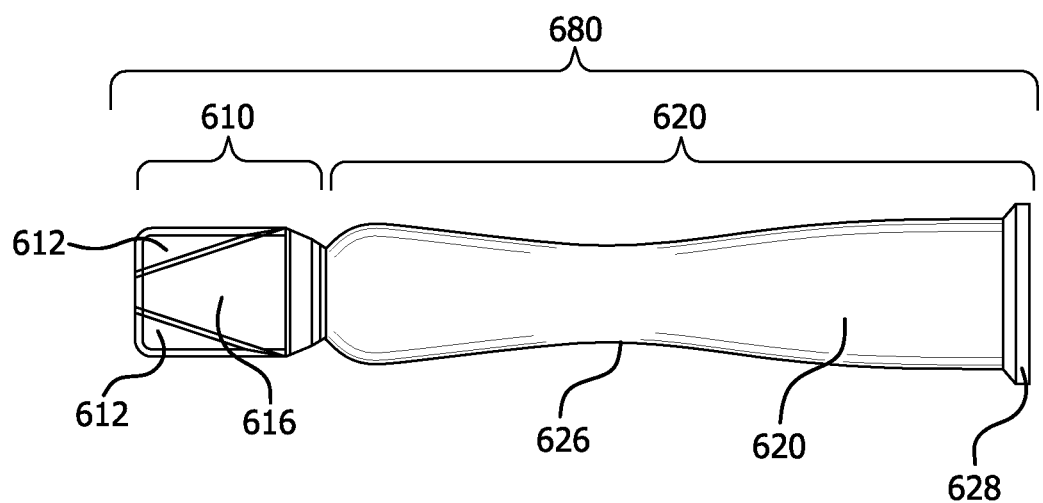
FIG. 8 is a perspective view of yet another embodiment of the present invention.
Figure 9:
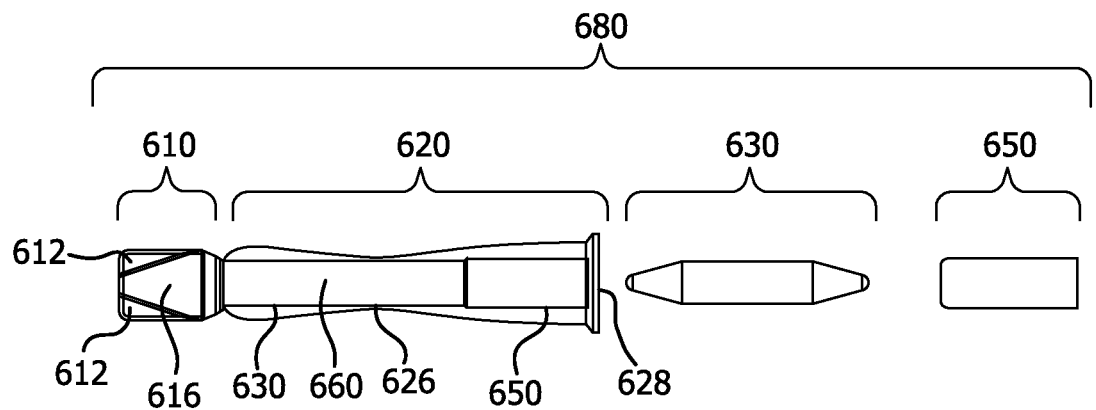
FIG. 9 is a perspective view of the component parts of the applicator embodied by FIG. 8.
Figure 10:
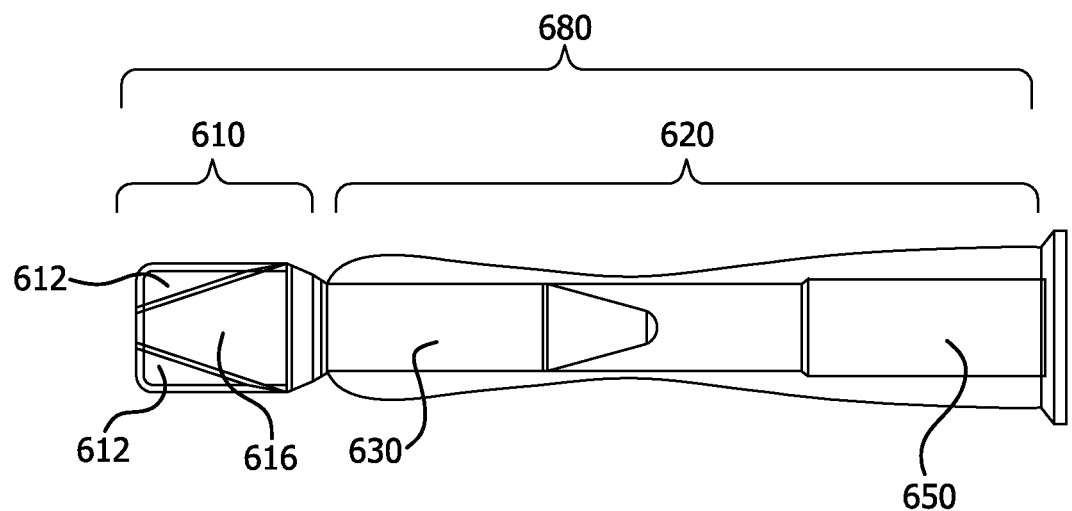
FIG. 10 is a cross-sectional view of the exemplary embodiment of FIG. 8.

FIGS. 8-10 illustrate yet another embodiment of the present invention. In this embodiment, applicator 680 comprises an applicator tip 610 and an applicator body 620, which includes an air space reducer 650 and a reservoir 630. The applicator tip is equipped with an applicator cap 612 to seal the opening of the applicator tip. A squeezing and grasping portion 626 is designed on the applicator body 620. An air space reducer 650 is designed to reduce the air space of the applicator body by altering the volume of air space needed so that the desired fill volume of the adhesive 660 can be provided. The back-end seal 628 is placed onto the applicator body 620 after the adhesive 660 is stored in the reservoir 630.

According to the embodiment of the present invention, the applicator 680 is activated when the applicator cap 612 is twisted or pulled off from the applicator tip 616. The adhesive 660 flows towards the open end of the applicator tip 616 to be applied on the substrate. Accordingly, in this embodiment there is no need to puncture a frangible container because the liquid adhesive is free-flowing within the applicator and, thus, activated once the cap 612 is removed.

The grasping portion 626 of the applicator body 620 is designed for both holding the applicator and controlling the flow rate of the adhesive. For comfort, a user may hold the grasping portion 626 as a pen with his/her thumb and index finger when the applicator is used to apply adhesive. The flow rate of adhesive 660 may be controlled by providing a constant but slow pressure on the grasping portion 626 of the applicator body 620. In certain embodiments, a desired amount of adhesive can be dispensed by applying a desired force to the grasping portion 626. The grasping portion 626 is generally made of semi-rigid material to permit controlled flow of the adhesive to the application site. Suitable materials include, but are not limited to, rubber, thermoplastics, thermosets, low density polyethylene, polypropylene, medium density polyethylene, high density polyethylene, or polyesters.

Dependent on the volume of the air space reducer 650, fill volume of the applicator reservoir 630 is in the range of about 0.1 mL to 20 mL, preferably about 0.2 mL to 15 mL, and more preferably about 0.2 mL to 10 mL. In order to inhibit premature polymerization, the volume of the applicator is preferably about 50 to 80 percent, and more preferably 60 to 80 percent, filled by the adhesive. The applicator body 620 may be constructed with suitable materials that have a desired barrier property for moisture and air so that the premature polymerization of the adhesive 660 can be prevented or inhibited. Suitable materials for the applicator body 620 include, but are not limited to, high density polyethylene (HDPE), polypropylene, polyvinylchloride, acrylonitrile copolymer, polycarbonate, polytetrafluoroethylene (PFTE), and polyethylene terephthalate (PET), polyvinylchloride, polystyrene (PS), polymethylpentene, and the like. In a preferred embodiment, the applicator body 620 is made of a thick layer of acrylonitrile copolymer. In another preferred embodiment, the applicator body 620 is made of multi-layer sheet material with acrylonitrile copolymer as the inner layer. Suitable acrylonitrile copolymers used to construct the applicator body 620 include those described previously in the first embodiment of the present invention.

In one embodiment, the back-end seal 628 of the applicator body 620 can be attached into the applicator body 620 with a screw cap or a snap cap. The tight connection between the back-end seal 628 and the applicator body 620 is designed to prevent leakage of the adhesive during use. Suitable materials for the back-end seal 628 include aluminum foil, plastic membrane, laminated aluminum foil, and multi-layer sheet materials. Multi-layer sheet materials may include, but are not limited to, high density polyethylene (HDPE), polypropylene, polyvinylchloride, acrylonitrile copolymer, polycarbonate, polytetrafluoroethylene (PFTE), polyethylene terephthalate (PET), polystyrene (PS), and polymethylpentene. Multi-layer sheet materials may be composed of at least two layers of such materials.

In embodiments, the applicator tip 616 is designed to connect to the applicator body 620 using the screw cap, snap-fit cap, or any other connection mechanism. The applicator tip 616 fits tightly into the applicator body to prevent re-opening of the connection as well as to prevent leakage of the adhesive material during use. The applicator tip may be a fibrous swab, a sponge swab, a foam tip, or a brush. The applicator tip may be composed of any of a variety of materials including foams, rubber, plastics, thermosets, films or membranes. The foam materials include, but are not limited to, polyolefin foam, polyether polyurethane foam, polyester polyurethane foam, and the like.

The applicator 680 is compatible with irradiation sterilization techniques such as Gamma sterilization, Electron beam sterilization and X-ray sterilization. The adhesive 660 stored in the applicator 680 can be sterilized by irradiation sterilization, which is not cured upon sterilization. In a more preferred embodiment, the adhesive 660 sterilized by irradiation sterilization technique in the applicator 680 may provide long term shelf life stability of at least about 12 months, and more preferably at least about 24 months.

The applicators of the present invention are used to apply adhesive materials. Preferred adhesives are readily polymerizable, i.e., anionically polymerizable and/or free radical polymerizable. The adhesive is preferably a 1,1-disubstituted ethylene monomer, e.g., a cyanoacrylate monomer. In a preferred embodiment, the adhesive materials of the present invention that may be packaged in said applicators are based upon one or more polymerizable cyanoacrylate monomers, and/or reactive oligmers of cyanoacrylate. Such cyanoacrylate monomers are readily polymerizable, e.g., anionically polymerizable and/or free radical polymerizable, to form polymers. Cyanoacrylate monomers suitable for use in accordance with the present invention include, but are not limited to, 1,1-disubstituted ethylene monomers of the formula:

$$HRC=CXY \qquad (I)$$

wherein X and Y are each strong electron withdrawing groups, and R is H, —CH=CH$_2$ or, provided that X and Y are both cyano groups, or a C$_1$-C$_4$ alkyl group.

Examples of monomers within the scope of formula (I) include alpha-cyanoacrylates, vinylidene cyanides, C$_1$-C$_4$ alkyl homologues of vinylidene cyanides, dialkyl methylene malonates, acylacrylonitriles, vinyl sulfinates and vinyl sulfonates of the formula CH$_2$=CX'Y wherein X' is —SO$_2$R' or —SO$_3$R' and Y' is —CN, —COOR=, —COCH$_3$, —SO$_2$R' or —SO$_3$R', and R' is H or hydrocarbyl.

Preferred monomers of formula (I) for use in this invention are alpha-cyanoacrylates. These monomers are known in the art and have the formula

(II)

wherein R$^2$ is hydrogen and R$^3$ is a hydrocarbyl or substituted hydrocarbyl group; a group having the formula —R$^4$—O—R$^5$—O—R$^6$, wherein R$^4$ is a 1,2-alkylene group having 2-4 carbon atoms, $R^5$ is an alkylene group having 2-12 carbon atoms, and $R^6$ is an alkyl group having 1-6 carbon atoms; or a group having the formula

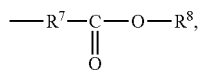

wherein $R^7$ is

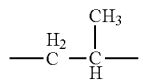

or $—C(CH_3)_2—$ or $—[C(CH_3)_2]_n—$ wherein n is 1-14, preferably 1-8 carbon atoms and $R^8$ is an organic moiety. Preferred alpha-cyanoacrylates are ones having an alkyl chain length of from about 1 to about 20 carbon atoms or more preferably from about 3 to about 8 carbon atoms. The preferred cyanoacrylates are n-butyl and 2-octyl cyanoacrylate, or mixtures thereof.

Examples of suitable hydrocarbyl and substituted hydrocarbyl groups include straight chain or branched chain alkyl groups having 1-16 carbon atoms; straight chain or branched chain $C_1$-$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms cycloalkyl groups; arylalkyl groups; alkylaryl groups; and aryl groups.

The organic moiety R8 may be substituted or unsubstituted and may be a straight chain, branched or cyclic, saturated, unsaturated or aromatic. Examples of such organic moieties include $C_1$-$C_8$ alkyl moieties, $C_2$-$C_8$ alkenyl moieties, $C_2$-$C_8$ alkynyl moieties, $C_3$-$C_{12}$ cycloaliphatic moieties, aryl moieties such as phenyl and substituted phenyl, and arylalkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 8 carbon atoms. In the cyanoacrylate monomer of formula (II), $R^8$ is preferably an alkyl group having 1-10 carbon atoms or a group having the formula -AO $R^9$, wherein A is a divalent straight or branched chain alkylene or oxyalkylene moiety having 2-8 carbon atoms, and R9 is a straight or branched alkyl moiety having 1-8 carbon atoms. The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, or a combination thereof.

Various applicators disclosed in the present invention may be used to apply adhesive materials to different substrates. Suitable substrates include, but are not limited to, living tissues, plastics, metals, wood, ceramics, fabrics, paper and the like. In preferred embodiments, the adhesive materials that are packaged in various applicators may be used as tissue adhesives for wound closure or as microbial sealant to prevent surgical site infection. For example, they can be used for closing surgical incisions, dressing traumatically lacerated tissues, dressing burns, covering superficial or skin surface wounds, and applying onto surgical incision site before surgery to provide in situ and post-surgery inhabitation of surgical site infections.

The adhesive materials that may be packaged in various applicators of the present invention may be bioabsorbable. The term "bioabsorbable" refers to polymers or medical devices that are able to completely degraded, eroded, and/or gradually absorbed or eliminated by the body when such polymers or medical devices are exposed to body fluid such as blood. The bioabsorbable adhesives can be used in many different applications including but not limited to general wound closure, endoscopic surgery, cardiac surgery, hernia surgery, artheroscopic surgery. Bioabsorbable adhesives are preferably based on cyanoacrylates. In embodiments of the present invention, a bioabsorbable adhesive composition is composed of alkoxyalkyl cyanoacrylate and polyethylene glycol. Said bioabsorbable adhesive compositions can also consist of the mixture of alkyl cyanoacrylate, alkoxyalkyl cyanoacrylate and polyethylene glycol. A preferred alkoxyalkyl cyanoacrylate is methoxyisopropyl cyanoacrylate. Other bioabsorbable adhesives may include copolymers of alkyl cyanoacrylate or alkoxyalkyl cyanoacrylate with other biocompatible monomers such as trimethylene carbonate, alkylene glycol, glycolide, lactide, ϵ-caprolactone, and dioxane.

In preferred embodiments of the present invention, the cyanoacrylate monomers can be prepared according to methods known in the art. Reference is made, for example, to U.S. Pat. Nos. 2,721,858 and 3,254,111, each of which is hereby incorporated by reference in its entirety. One such process includes, for example, reacting a cyanoacetate with formaldehyde in the presence of a basic condensation catalyst at an elevated temperature to produce a low molecular weight polymer. A de-polymerization (or cracking) step is followed under high temperature and high vacuum in the presence of acidic and anionic inhibitors, yielding a crude monomer that can be distilled under high temperature and high vacuum in the presence of radical and acidic inhibitors.

Various applicators disclosed herein are compatible with irradiation sterilization techniques such as electron beam sterilization, gamma sterilization, and/or X-ray sterilization. The preferred containers for cyanoacrylate adhesives are made of acrylonitrile copolymers or multi-layer sheet materials with acrylonitrile copolymer as the inner layer to contact cyanoacrylate adhesives. Such materials are irradiation stable under the maximum dosage of e-beam, gamma, and X-ray sterilization. The exceptional barrier properties offered by acrylonitrile copolymer make it an ideal inner layer material for use in construction of package bodies, in accordance with the present invention, to sterilize adhesive compositions using irradiation sterilization techniques. The inner layer of acrylonitrile copolymer provides high barrier properties which ensure the stability of the liquid adhesive compositions stored therein. Acrylonitrile copolymer offers a high barrier to oxygen at all levels of relative humidity. This ensures that a consistently high barrier to oxygen is maintained, regardless of the humidity of the surrounding environment. In addition, the water vapor barrier properties of acrylonitrile copolymer are comparable to other plastic packaging materials and are ultimately enhanced by the outer layer secured thereto in accordance with the present invention. All of the properties of acrylonitrile copolymer enable it to be a suitable material as the package body for sterilizing cyanoacrylates via irradiation sterilization technique.

The dose of irradiation applied should be sufficient enough to sterilize both the applicator and the adhesive inside. In embodiments, the e-beam irradiation can be in a suitable dosage of from about 5 to 50 kGy, preferably from about 10 to about 30 kGy, and more preferably from about 12 to about 25 kGy. The dose of X-ray applied to the adhesive stored in said applicators is in the range of 5 kGy to 40 kGy, preferably in the range of about 5 kGy to 30 kGy, more preferably about 5 kGy to 25 kGy. Gamma irradiation for the adhesives packaged in the preferred applicators can be in a suitable dosage of from about 5 to 50 kGy, preferably about 5 to about 40 kGy, and more preferably from about 5 to 25 kGy.

The adhesive stored in various applicators in the present invention is not cured and polymerized upon e-beam, gamma, or X-ray sterilization. In more preferred embodiments, the adhesive materials provide a stable shelf life for use in the medical field. For example, the adhesive in said applicators after irradiation sterilization may provide a shelf life of at least 12 months, more preferably at least 24 months. The shelf life stability of liquid adhesive compositions in various said applicators sterilized by different irradiation sterilization techniques may be evaluated by an accelerated aging study at 80° C. The study was performed in an oven at 80° C. for a period of 13 days. Based on ASTM F19802, 13 days accelerated aging at 80° C. correlates to 2 years of shelf life at ambient temperatures, and 1 day of accelerated aging at 80° C. is equal to 56 days at ambient temperature.

In order to reduce the bioburden, the cyanoacrylate adhesive compositions stored in various applicators disclosed herein may be filtered through a 0.2 µm filter prior to different irradiation sterilizations. The preferred applicators with the secondary packaging may also be sterilized with heat and/or ethylene oxide prior to the final irradiation.

A sterility assurance level (SAL) should be obtained at a minimum of $10^{-3}$, which means that the probability of a single unit being non-sterile after sterilization is 1 in 1000. In more preferred embodiments, the sterility assurance level may be at least $10^{-6}$. The sterility of the cyanoacrylate adhesives packaged in various applicators after irradiation sterilization may be analyzed by Bacteriostasis and Fungistasis tests. After testing with challenging microorganisms such as *Bacillus subtilis, Candida albicans*, and *Aspergillus niger*, no growth of the microorganisms for the cyanoacrylate adhesive in said applicators after irradiation sterilization indicates the sterility of the cyanoacrylate adhesive.

The cyanoacrylate monomers may be stabilized by using a combination of free radical and anionic stabilizers before storing into the various applicators of the present invention. Suitable free radical stabilizers include without limitation; butylated hydroxy anisole (BHA); hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3methoxyphenol; 2-tert-butyl-4methoxyphenol; and 2,2-methylene-bis-(4-methyl-6-tert-butylphenol). The stabilizers may be present in an amount of 200 ppm to 15000 ppm, preferably 1000 ppm to 10000 ppm, and more preferably 2000 ppm to 8000 ppm.

Suitable anionic stabilizers for adhesives stored in said various applicators may include, but are not limited to, perchloric acid, hydrochloric acid, hydrobromic acid, sulfur dioxide, toluenesulfonic acid, fluorosulfonic acid, phosphoric acid, ortho, meta, or para-phosphoric acid, trichloroacetic acid, and sulfuric acid. The anionic stabilizer may be present in an amount of about 2 ppm to about 500 ppm, preferably about 10 ppm to about 200 ppm.

In embodiments, the cyanoacrylate adhesive in various applicators may further contain small amounts of colorants such as dyes or pigments. Suitable dyes include derivatives of anthracene and other complex structures, specifically, without limitation, 1-hydroxy-4-[4-methylphenylamino]-9,10 anthracenedione (D&C violet No. 2); 9-(ocarboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); 2-(1,3dihydro-3-oxo-5-sulfo-2H-indole-2-ylidine)-2,3-dihydro-3oxo-1H-ind-ole-5 sulfonic acid disodium salt (FD&C Blue No. 2); and 1,4-bis(4methylanilino)anthracene-9,10-dione (D&C Green No. 6). The preferred dyes are D&C Violet No. 2, FD&C Blue No. 2, and D&C Green No. 6.

A polymerization accelerator may be included in the cyanoacrylate adhesive materials stored in various applicators disclosed herein. Suitable polymerization accelerators may include, but are not limited to, calixarenes and oxacalixarenes, silacrowns, crownethers, cyclodextrin and its derivatives, polyethers, aliphatic alcohol, various aliphatic carboxylic acid esters, benzoyl peroxide, amine compounds such as are triethyl amine, diethyl amine, butyl amine, isopropyl amine, tributyl amine, N,N,-dimethyl aniline, N,N-diethyl aniline, N,N-dimethyl-p-toluidine, N,N-dimethyl-m-toluidine, N,Ndimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts, ether-bonded ammonium salts and alkylimidazolinium salts, cyclosulfur compounds and derivatives, and polyalkylene oxides and derivatives.

In embodiments of the present invention, the cyanoacrylate adhesive compositions in various applicators disclosed herein may optionally comprise an antimicrobial agent in an effective amount. The antimicrobial agent is released from the polymer film of the adhesives formed on human or animal skins to inhibit microbial growth and prevent wound or surgical site infections. Suitable antimicrobial agents include, but are not limited to, antibacterial agents such as chlorhexidine and its salts, typical antibiotics, copolymers of vinylpyrrolidone and vinyl acetate, antiseptics, the iodine containing polymer such as povidone iodine, biguanidine compounds, phenol compounds such as 5-chloro-2-(2,4-dichlorophenoxy)phenol, acridine compounds, quaternary ammonium compounds such as benzalkonium chloride, cetylpridospores and zephiran, copolymers of vinylpyrrolidone and vinyl acetate cross-linked with polyisocyanates, heavy metal salts such as silver nitrate, and aldehyde compounds such as glutaraldhyde.

The cyanoacrylate adhesive in various applicators disclosed herein may optionally contain thickening agents. Suitable thickening agents include, but are not limited to, polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, and triblock copolymers of polyoxypropylene flanked by two hydrophilic chains of polyoxyethylene. Preferred thickening agents include a partial polymer of cyanoacrylate as disclosed in U.S. patent application Pub. No. 2009/0318583, and triblock copolymers of polyoxyalkylene as disclosed in U.S. patent application Pub. No. 2009/0317353. Preferably the thickening agent is miscible in cyanoacrylate monomer compositions at room temperature.

The cyanoacrylate adhesive in various applicators in the present invention may optionally include at least one plasticizing agent that imparts flexibility to the polymer formed from the monomer. The plasticizing agent preferably does not contain any moisture and should not adversely affect the stability of said cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl) phosphate, tri(p-cresyl) phosphate, diisodecyl adipate (DIDA), glyceryl triacetate, glyceryl tributyrate, dioctyl adipate (DICA), isopropyl myrisate, butyl sterate, lauric acid, trioctyl trimelliate, dioctyl glutatrate (DICG) and mixtures thereof. Tributyl citrate, diisodecyl adipate and acetyl tributyl citrate are preferred plasticizers, which when present are in an amount of up to thirty percent (30%) by weight of the liquid adhesive composition The amount to be used can be determined by one of ordinary skills in the art, using known techniques without undue experimentation.

The cyanoacrylate adhesive packaged in said applciator may also optionally include preservatives. A preservative may be paraben such as alkyl parabens and salts thereof, ethylparaben, methylparaben, methylparaben sodium, propylparaben sodium, propylparaben, butylparaben, and the like. Other suitable preservatives include hydroquinone, pyrocatechol, resorcinol, 4-n-hexyl resorcinol, benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, cresols, phenylmercuric compounds such as phenylmercuric borate, and phenylmercuric nitrate.

What is claimed is:

1. An applicator, comprising:
an adhesive comprising a cyanoacrylate monomer, a free radical stabilizer in an amount of about 2000 ppm to about 8000 ppm, an anionic stabilizer in an amount of about 10 ppm to about 200 ppm, optionally a polymerization accelerator, and optionally a plasticizing agent,
a body comprising a porous applicator tip, a cutter for breaking a frangible seal on a container containing the adhesive, a channel through which the adhesive flows toward the porous applicator tip, a chamber for housing the container, the chamber in fluid communication with the channel, and a flexible grip for controlling the flow rate of the adhesive through the channel, and
a container comprising an acrylonitrile copolymer or a multi-layer sheet with an acrylonitrile copolymer as the inner-most layer of the sheet, and comprising a frangible seal on one end, thereby containing the adhesive within the container, the container inserted into and being movable within the chamber of the body,
wherein at least the container is sterilized by irradiation, and the adhesive contained within the container does not cure upon irradiation and for at least twelve months of shelf storage thereafter.

2. The applicator according to claim 1, wherein the acrylonitrile copolymer comprises acrylonitrile and methyl acrylate.

3. The applicator according to claim 1, wherein the irradiation comprises electron beam, gamma, or X-ray irradiation.

4. The applicator according to claim 1, wherein the adhesive contained within the container does not cure for at least 24 months of shelf storage after irradiation.

5. The applicator according to claim 1, wherein the cyanoacrylate monomer is selected from the group consisting of 2-octylcyanoacrylate, n-butyl cyanoacrylate, a mixture of 2-octyl cyanoacrylate and n-butyl cyanoacrylate, and methoxyisopropyl cyanoacrylate.

6. An applicator, comprising:
an adhesive comprising a cyanoacrylate monomer, a free radical stabilizer in an amount of about 2000 ppm to about 8000 ppm, an anionic stabilizer in an amount of about 10 ppm to about 200 ppm, optionally a polymerization accelerator, and optionally a plasticizing agent,
a body comprising a porous applicator tip, a cutter having an opening on each end and a channel between each opening and through the cutter, through which the adhesive flows into a reservoir, the reservoir in fluid communication with the channel and the porous applicator tip, and a flexible grasping portion for controlling the flow rate of the adhesive through the reservoir,
a container comprising an acrylonitrile copolymer or a multi-layer sheet with an acrylonitrile copolymer as the inner-most layer of the sheet, and comprising a frangible seal on one end, thereby containing the adhesive within the container, the container inserted into and being movable within the reservoir of the body; and
a container mount, onto which the container is attached via the end of the container that does not comprise the frangible seal,
wherein at least the container is sterilized by irradiation, and the adhesive contained within the container does not cure upon irradiation and for at least twelve months of shelf storage thereafter.

7. The applicator according to claim 6, wherein the acrylonitrile copolymer comprises acrylonitrile and methyl acrylate.

8. The applicator according to claim 6, wherein the the irradiation comprises electron beam, gamma or X-ray irradiation.

9. The applicator according to claim 6, wherein the adhesive contained within the container does not cure for at least 24 months of shelf storage after irradiation.

10. The applicator according to claim 6, wherein the applicator tip comprises a fibrous swab, a sponge, a foam tip, or a brush.

11. The applicator according to claim 6, wherein the cyanoacrylate monomer is selected from the group consisting of 2-octylcyanoacrylate, n-butyl cyanoacrylate, a mixture of 2-octyl cyanoacrylate and n-butyl cyanoacrylate, and methoxyisopropyl cyanoacrylate.

12. An applicator, comprising:
an adhesive comprising a cyanoacrylate monomer, a free radical stabilizer in an amount of about 2000 ppm to about 8000 ppm, an anionic stabilizer in an amount of about 10 ppm to about 200 ppm, optionally a polymerization accelerator, and optionally a plasticizing agent,
a body comprising an applicator tip selected from the group consisting of a fibrous swab, a sponge swab, foam, and a brush, a container comprising an acrylonitrile copolymer or a multi-layer sheet with an acrylonitrile copolymer as the inner-most layer of the sheet, and comprising a seal on the back end of the container for sealing the adhesive within the container, an air space reducer between the adhesive and the back end seal, and a grasping portion for controlling the flow rate of the adhesive through the body; and
a removable cap covering the applicator tip, wherein the applicator is sterilized by irradiation, and the adhesive contained within the container does not cure upon irradiation and for at least twelve months of shelf storage thereafter.

13. The applicator according to claim 12, wherein the acrylonitrile copolymer comprises acrylonitrile and methyl acrylate.

14. The applicator according to claim 12, wherein the irradiation comprises electron beam, gamma, or X-ray irradiation.

15. The applicator according to claim 12, wherein the adhesive contained within the container does not cure for at least 24 months of shelf storage after irradiation.

16. The applicator according to claim 1 further comprising a finger stopper.

17. The applicator according to claim 12, wherein the cyanoacrylate monomer is selected from the group consisting of 2-octylcyanoacrylate, n-butyl cyanoacrylate, a mixture of 2-octyl cyanoacrylate and n-butyl cyanoacrylate, and methoxyisopropyl cyanoacrylate.

* * * * *